(12) United States Patent
Zagorchev et al.

(10) Patent No.: US 12,257,096 B2
(45) Date of Patent: Mar. 25, 2025

(54) PATIENT-SPECIFIC INFUSION COVERAGE ESTIMATES USING SEGMENTED 3D BRAIN REPRESENTATIONS

(71) Applicant: ClearPoint Neuro, Inc., Solana Beach, CA (US)

(72) Inventors: Lyubomir Zagorchev, Burlington, MA (US); Damon Hyde, Somerville, MA (US); Chen Li, Plainfield, OH (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 399 days.

(21) Appl. No.: 17/894,589

(22) Filed: Aug. 24, 2022

(65) Prior Publication Data

US 2024/0065662 A1 Feb. 29, 2024

(51) Int. Cl.
*A61B 6/00* (2024.01)
*A61B 34/20* (2016.01)

(52) U.S. Cl.
CPC .............. *A61B 6/541* (2013.01); *A61B 34/20* (2016.02); *A61B 2034/2051* (2016.02)

(58) Field of Classification Search
CPC .. A61B 6/541; A61B 34/20; A61B 2034/2051
USPC ......................................................... 382/128
See application file for complete search history.

(56) References Cited

U.S. PATENT DOCUMENTS

| | | | | |
|---|---|---|---|---|
| 7,432,924 | B2* | 10/2008 | Ohishi | A61B 6/481 |
| | | | | 382/128 |
| 8,165,371 | B2* | 4/2012 | Bi | G01R 33/5635 |
| | | | | 382/128 |
| 2014/0303486 | A1* | 10/2014 | Baumgartner | A61B 5/055 |
| | | | | 600/414 |
| 2023/0089375 | A1* | 3/2023 | Okuda | G06T 7/38 |
| | | | | 382/128 |

* cited by examiner

*Primary Examiner* — Allen H Nguyen
(74) *Attorney, Agent, or Firm* — Sheppard Mullin Richter & Hampton LLP

(57) ABSTRACT

Systems and methods provide automated systems for accurately estimating infusion coverage within a target brain region in real-time (or approximately real-time) during surgical procedures. Such accurate and real-time infusion coverage estimation enables intraoperative monitoring and adjustment of infusion parameters (e.g., cannula tip location, infusate delivery flow rate, etc.) for achieving optimal/improved infusion coverage for a given drug therapy. Accordingly, examples of the presently disclosed technology can improve the efficacy and safety of drug therapies delivered to the brain.

20 Claims, 5 Drawing Sheets

```
┌─────────────────────────────────┐
│   COMPARE A FIRST 3D IMAGE OF A │
│ PATIENT'S BRAIN BEFORE INFUSATE │
│  HAS BEEN DELIVERED TO THE      │
│  PATIENT'S BRAIN TO A SECOND 3D │
│  IMAGE OF THE PATIENT'S BRAIN   │
│  AFTER INFUSATE HAS BEEN        │
│  DELIVERED TO THE PATIENT'S     │
│              BRAIN 402          │
└─────────────────────────────────┘

┌─────────────────────────────────┐
│  GENERATE A 3D INFUSATE         │
│  DELIVERY REPRESENTATION BASED  │
│  ON THE IMAGE COMPARISON 404    │
└─────────────────────────────────┘

┌─────────────────────────────────┐
│  COMPARE THE 3D INFUSATE        │
│  DELIVERY REPRESENTATION TO A   │
│  SEGMENTED 3D REPRESENTATION    │
│  OF THE PATIENT'S BRAIN THAT    │
│  INCLUDES A 3D TARGET BRAIN     │
│  REGION SUB-REPRESENTATION      │
│  REPRESENTING A TARGET BRAIN    │
│             REGION 406          │
└─────────────────────────────────┘

┌─────────────────────────────────┐
│  BASED ON THE 3D REPRESENTATION │
│  COMPARISON, ESTIMATE A LEVEL   │
│  OF COVERAGE FOR DELIVERED      │
│  INFUSATE WITHIN THE TARGET     │
│         BRAIN REGION 408        │
└─────────────────────────────────┘

┌─────────────────────────────────┐
│  PROVIDE A NOTIFICATION RELATED │
│  TO THE ESTIMATED LEVEL OF      │
│  COVERAGE FOR DELIVERED         │
│  INFUSATE WITHIN THE TARGET     │
│         BRAIN REGION 410        │
└─────────────────────────────────┘
```

Fig. 4

PATIENT-SPECIFIC INFUSION COVERAGE ESTIMATES USING SEGMENTED 3D BRAIN REPRESENTATIONS

TECHNICAL FIELD

The present disclosure relates generally to medical technologies, and more particularly, some examples relate to estimating infusion coverage for drug therapies delivered to the brain.

BACKGROUND

Drug therapies delivered to the brain can treat various genetic and acquired brain diseases. Delivering these therapies typically involves using a targeting cannula to administer/deliver infusate (i.e., drug) at one or more infusion points within a target brain region (i.e., a brain region targeted for therapy). Depending on the drug therapy and/or target brain region (e.g., tissue properties and local geometry of the target brain region), infusate coverage within the target brain region (i.e., the extent to, and manner in which, delivered infusate is volumetrically distributed within the target brain region) can be a crucial factor for optimizing/improving the efficacy and safety of the drug therapy. For example, a given drug therapy may be most effective when a particular volume of infusate is distributed uniformly across an entire target brain region.

Various infusion parameters may influence infusate coverage within a target brain region, including infusate flow rate (infusate flow rate may be controlled by an infusion pump which pushes infusate through the targeting cannula into the brain), targeting cannula tip/infusion point location, etc. For example, broader infusate coverage can be achieved by delivering infusate at multiple infusion points along a surgical trajectory within the target brain region. The delivered infusate may then flow/spread to larger volumes of the target brain region.

BRIEF DESCRIPTION OF THE DRAWINGS

The present disclosure, in accordance with one or more various examples, is described in detail with reference to the following figures. The figures are provided for purposes of illustration only and merely depict examples.

FIG. 4 depicts an example flow diagram that may be used to estimate a level of coverage for infusate delivered to a target brain region, in accordance with various examples of the presently disclosed technology.

Figure 1:
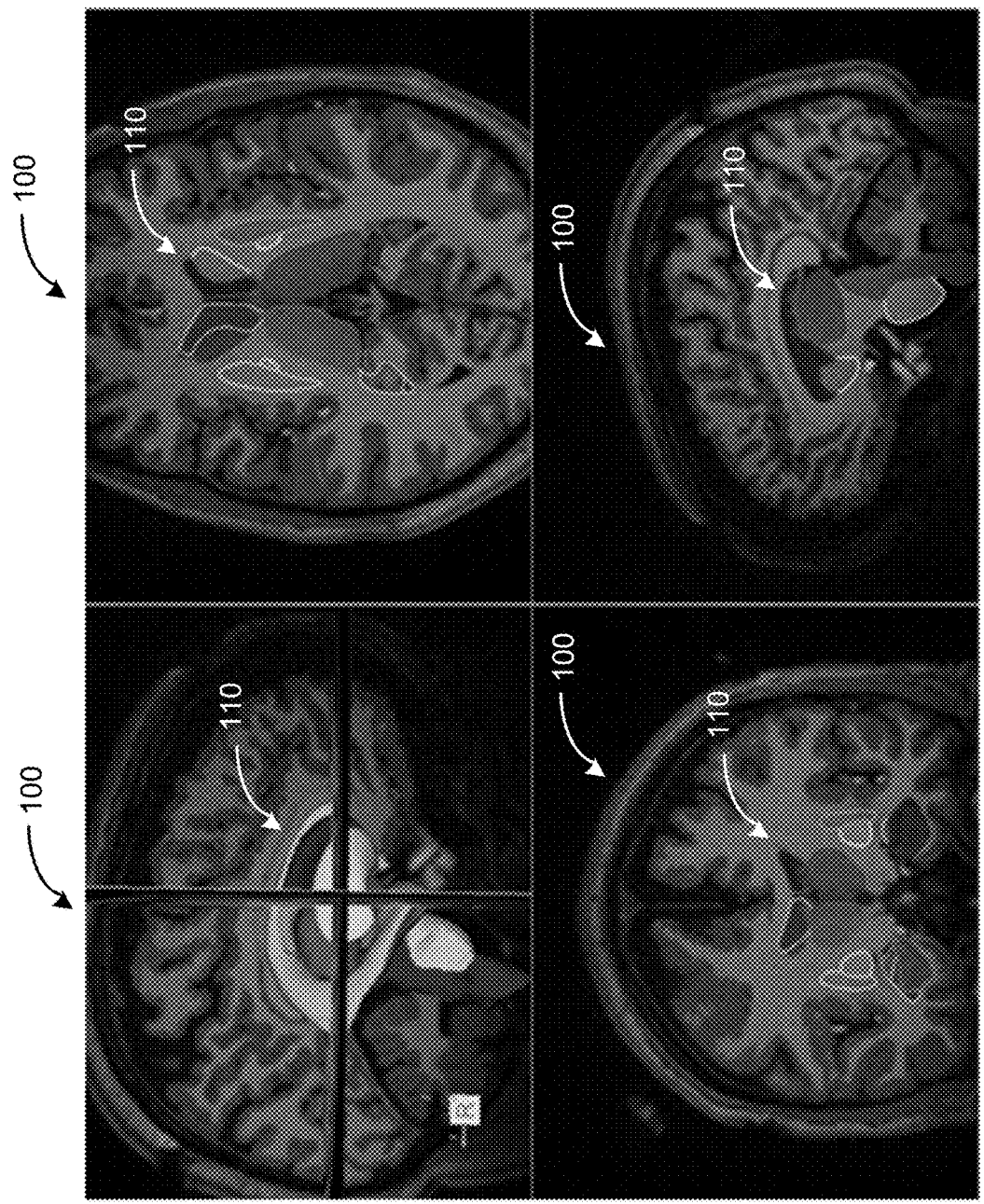
FIG. 1 depicts an example patient-specific segmented 3D brain representation, in accordance with various examples of the presently disclosed technology.

The figures are not exhaustive and do not limit the present disclosure to the precise form disclosed.

DETAILED DESCRIPTION

As described above, infusate coverage within a target brain region can be a crucial factor for optimizing/improving the efficacy and safety of a drug therapy. Accordingly, real-time (as used herein "real-time" may refer to approximate "real-time" as well) visualization of infusion coverage within a target brain region would present a tremendous opportunity for optimizing/improving the efficacy and safety of drug therapies delivered to the brain. For example, such real-time visualization could enable intraoperative monitoring and adjustment of infusion parameters (e.g., cannula tip location, infusate delivery flow rate, etc.) to achieve optimal/improved infusion coverage for a given drug therapy.

Unfortunately, existing technologies are largely incapable of accurate, real-time estimation of infusion coverage within a target brain region. Accordingly, neurosurgeons typically rely on their own visual assessment of inter-operative images/scans (e.g., MRI scans or CT scans obtained during an infusion procedure) to gauge infusion coverage. This manual approach can be subjective and highly inaccurate. In addition, current visualizations of infusate coverage (e.g., inter-operative MRI or CT scans) typically hide structural boundaries of brain structures (including a target brain region), significantly complicating visual assessment during an infusion.

As described above, poor infusion coverage estimation can result in sub-optimal infusion coverage, which may lead to ineffective/unsafe drug therapies or failed clinical trials. Relatedly, because existing technologies struggle to estimate patient-specific infusion coverage in real-time, neurosurgeons typically rely on standardized (i.e., non-patient specific) clinical protocols to define infusion parameters for a given drug therapy. Because infusion parameters (e.g., infusion flow rates) can vary from person-to-person, brain region-to-brain region, procedure-to-procedure, etc.—these standardized clinical protocols can lead to sub-optimal infusion coverage for particular patients/procedures, which again may lead to ineffective and/or unsafe drug therapies.

Against this backdrop, examples of the presently disclosed technology provide automated systems and methods for accurately estimating infusion coverage within a target brain region in real-time during surgical procedures. Such accurate and real-time infusion coverage estimation enables intraoperative monitoring and adjustment of infusion parameters (e.g., cannula tip location, infusate delivery flow rate, etc.) for achieving optimal/improved infusion coverage for a given drug therapy. Accordingly, examples of the presently disclosed technology can improve the efficacy and safety of drug therapies delivered to the brain.

Examples of the presently disclosed technology can automatically estimate infusion coverage in a target brain region by (1) subtracting a first 3D image of a patient's brain (e.g., a first MRI or CT image) acquired before infusate has been delivered to the patient's brain from a second 3D image of the patient's brain (e.g., a second MRI or CT image) acquired after infusate has been delivered to the patient's brain; (2) based on the subtraction, generating a 3D infusate delivery representation that volumetrically represents the delivered infusate within the patient's brain; (3) comparing the 3D infusate delivery representation to a "segmented" 3D representation of the patient's brain that includes a 3D segment/sub-representation representing the target brain region (i.e., a 3D target brain structure sub-representation); and (4) based on the comparison, estimating a level of coverage for delivered infusate within the target brain region.

As will be described in greater detail below, the segmented 3D representation of the patient's brain may be a computerized 3D representation of the patient's brain comprised of individual 3D segments/sub-representations representing various regions/structures of the patient's brain (e.g., sub-cortical structures such as the putamen, thalamus, etc.). Accordingly, the segmented 3D representation of the patient's brain may identify—within the computerized 3D representation of the patient's brain—the various brain regions/structures of the patient, including the target brain region. Thus, by comparing the 3D infusate delivery representation to the segmented 3D representation of the patient's brain—which includes the 3D target brain structure sub-representation—examples can estimate a volume for delivered infusate within the target brain region. In certain examples, such comparison may comprise combining/overlaying the 3D infusate delivery representation and the segmented 3D representation of the patient's brain (which again, includes the 3D target brain structure sub-representation). Accordingly, examples can estimate the volume for delivered infusate within the target brain region based on an amount of overlap between the 3D infusate delivery representation and the 3D target brain structure sub-representation after they have been combined/overlaid. In various instances, examples can measure the amount of overlap between the 3D infusate delivery representation and the 3D target brain structure sub-representation by counting a number of voxels shared by the 3D infusate delivery representation and the 3D target brain region sub-representation. Conversely, examples can estimate a volume of infusate delivered outside of the target brain region by counting a number of voxels of the 3D infusate delivery representation that are not shared with the 3D target brain region sub-representation.

Utilizing techniques described above, examples can estimate infusion coverage within a target brain region and provide notifications to a neurosurgeon which visualize estimated infusion coverage in real-time. For instance, examples may visualize estimated infusion coverage using a "traffic light" notion: i.e., red (i.e., complete coverage achieved/stop infusion), yellow (i.e., nearly complete coverage achieved/continue infusion with caution), and green (i.e., incomplete infusion coverage/continue infusion). Here, infusion can be stopped when a certain percentage of coverage for the targeted brain region has been achieved.

As described above, by providing accurate, real-time infusion coverage estimations, examples of the presently disclosed technology can improve the efficacy and safety of drug therapies delivered to the brain in numerous ways. For instance, examples improve accuracy and responsiveness for inter-operative monitoring, which can allow a neurosurgeon to adjust infusion parameters more intelligently during an infusion procedure. Relatedly, examples may be used to change the current practice of setting up fixed clinical protocols for pharma trials. Optimal dosage of delivered infusate/therapeutic can and should be estimated during a pharmaceutical trail based on patient-specific data. Accordingly, infusion coverage estimates of the presently disclosed technology can reduce variability in current practice for pharmaceutical trials, thereby improving their safety and efficacy. In addition, examples can also estimate a volume of delivered infusate located outside of a target brain region (i.e., infusate which is not staying within the intended target brain region). In many cases, delivered infusate located/leaking outside of a target brain region can lead to unsafe outcomes. Accordingly, by visualizing/estimating a volume of infusate delivered outside of a target brain region in real-time, examples of the presently disclosed technology enable inter-operative adjustment of infusion parameters to reduce further infusate leaking.

FIG. 1 depicts an example patient-specific segmented 3D brain representation 100, in accordance with various examples of the presently disclosed technology. As will be described below, patient-specific segmented 3D brain representation 100 may be a computerized 3D representation of a patient's brain comprised of individual 3D segments/sub-representations representing various regions/structures of the patient's brain (e.g., sub-cortical structures such as the putamen, thalamus, etc.). Patient-specific segmented 3D brain representation 100 can be based on imaging data (e.g., MRI or CT scans) of the patient's brain.

Patient-specific 3D brain representation 100 may comprise various 3D segments/sub-representations that represent structures/regions of the patient's brain. In the specific example of FIG. 1, patient-specific segmented 3D brain representation 100 includes 3D target brain region sub-representation 110 (i.e., a sub-representation of patient-specific segmented 3D brain representation 100). Here, the target brain region (represented by 3D target brain region sub-representation 110) may be a region of the patient's brain targeted for drug/infusate delivery. The target brain region may be a specific brain structure (e.g., a sub-cortical structure such as the putamen, thalamus, etc.), a portion/segment of a specific brain structure, or a more general region/volume of the patient's brain.

Examples can generate patient-specific segmented 3D brain representations (e.g., patient-specific segmenting 3D brain representation 100) by adapting a generalized segmented 3D brain representation (i.e., a non-patient-specific segmented 3D representation of the human brain) to patient-specific brain image data commonly acquired in clinical settings (e.g., MRI or CT scans of a patient's brain obtained before or during an infusion procedure). In this way, examples of the presently disclosed technology can be easily reproduced across different patients, procedures, sites, etc. Accordingly, examples of the presently disclosed technology may improve upon existing infusion coverage estimation methodologies which are not as easily reproducible.

In certain examples, the generalized segmented 3D brain representation described above may comprise a 3D mesh representation. A mesh (or surface mesh) may refer to a representation of a larger domain (e.g., a volume or surface) comprised of smaller discrete cells called mesh elements, and mesh vertices at the junctions of adjacent/adjoining mesh elements. Meshes can be used to compute solutions to equations across individual mesh elements, which then can be used to approximate solutions over the larger domain. For example, meshes can be used to compute volumes contained within 3D closed mesh boundary surfaces.

By adapting a generalized segmented 3D (mesh) brain representation to imaging data of the patients' brain, examples can generate patient-specific segmented 3D (mesh) brain representations. These patient-specific segmented 3D (mesh) brain representations may preserve point-based correspondences between mesh vertices of the generalized segmented 3D (mesh) brain representation and mesh vertices of the patient-specific segmented 3D (mesh) brain representations. Such preservation can be used to establish point-based correspondences for target brain regions (e.g., the target brain region represented by 3D target brain region sub-representation 110) for therapy delivery across varied populations.

Referring again to FIG. 1, patient-specific segmented 3D brain representation 100 may comprise a 3D mesh representation. In these examples, the various 3D segments/sub-representations of patient-specific segmented 3D brain representation 100 (e.g., 3D target brain region sub-representation 110) may be represented as 3D closed mesh boundary surfaces comprised of mesh elements and mesh vertices (the volumes of these 3D closed mesh boundary surfaces may comprise mesh elements and mesh vertices as well). As will be described below, examples can estimate a volume for a target brain region by computing a volume for a 3D closed mesh boundary surface (e.g., 3D target brain region sub-representation 110) representing the target brain region. This estimated volume for the target brain region can be compared to an estimated volume for infusate delivered to the target brain region to estimate a level of coverage for delivered infusate within the target brain region.

Figure 2:
FIG. 2 depicts another example patient-specific segmented 3D brain representation, in accordance with various examples of the presently disclosed technology.

FIG. 2 depicts an example patient-specific segmented 3D brain representation 200, in accordance with various examples of the presently disclosed technology. Like patient-specific segmented 3D brain representation 100, patient-specific segmented 3D brain representation 200 comprises a 3D segment/sub-representation for a target brain region (i.e., 3D target brain region sub-representation 210). Here patient-specific segmented 3D brain representation 200 and 3D target brain region sub-representation 210 may be the same/similar as patient-specific segmented 3D brain representation 100 and 3D target brain region sub-representation 110 respectively. As depicted, patient-specific segmented 3D brain representation 200 and 3D target brain region sub-representation 210 may comprise 3D mesh representations.

As depicted in FIG. 2, a targeting cannula 250 may be used to deliver infusate to the target brain region represented by 3D target brain region sub-representation 210.

Figure 3:
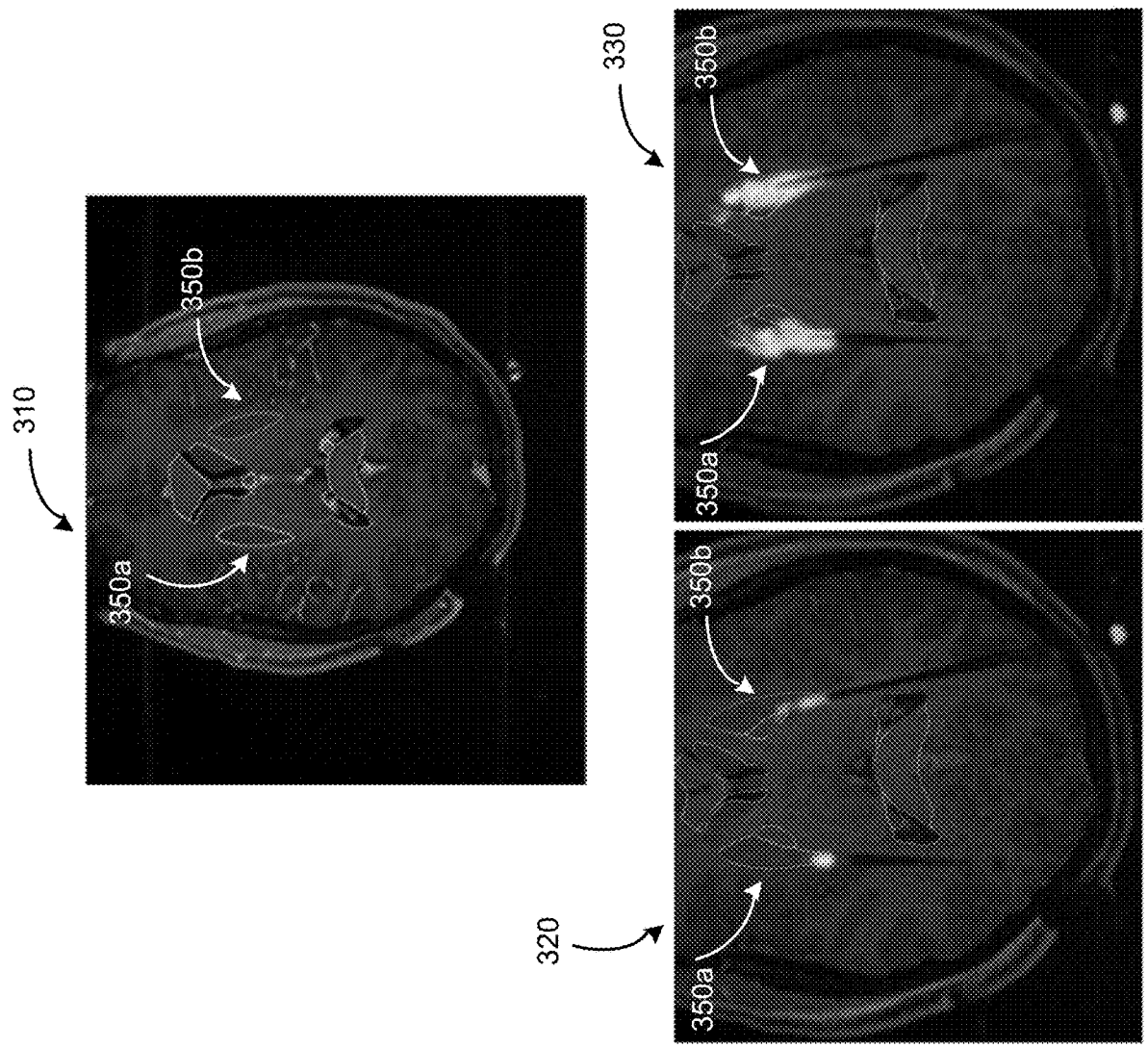
FIG. 3 depicts three example inter-operative images obtained from an example infusion procedure, in accordance with various examples of the presently disclosed technology.

FIG. 3 depicts three example inter-operative images obtained from an example infusion procedure, in accordance with various examples of the presently disclosed technology. Each inter-operative image may be an image acquired during the example infusion procedure.

For example, inter-operative image 310 may be a first image (e.g., an MRI or CT scan) of a patient's brain acquired before infusate has been delivered. Inter-operative image 320 may be a second image of the patient's brain acquired after a first amount of infusate has been delivered to target brain regions 350*a* and 350*b* (here inter-operative image 320 may have been acquired after inter-operative image 310). Inter-operative image 330 may be a third image of the patient's brain acquired after a second amount of infusate has been delivered to target brain regions 350*a* and 350*b* (here inter-operative image 330 may have been acquired after inter-operative image 320).

As alluded to above, examples of the presently disclosed technology can generate 3D infusate delivery representations by comparing inter-operative images 310-330 to each other. In various examples, such comparisons may comprise subtracting inter-operative image 310 (i.e., the baseline/pre-infusate delivery image) from the subsequent inter-operative images acquired after infusate has been delivered to the patient's brain. For instance, examples may subtract inter-operative image 310 from inter-operative image 320 to generate a first 3D infusate delivery representation that volumetrically/spatially represents the first amount of infusate delivered to target brain regions 350*a* and 350*b*. Similarly, examples may subtract inter-operative image 310 from inter-operative image 330 to generate a second 3D infusate delivery representation that volumetrically/spatially represents the second amount of infusate delivered to target brain regions 350*a* and 350*b*.

As described above, examples can utilize these 3D infusate delivery representations to track/visualize infusion coverage during the infusion procedure in real-time. In particular, by comparing the 3D infusate delivery representations to a patient-specific segmented 3D brain representation examples can automatically estimate (1) a volume of infusate delivered within target brain regions 350*a* and 350*b*—and by extension—a level of infusion coverage within target brain regions 350*a* and 350*b*, and/or (2) a volume of delivered infusate located outside of target brain regions 350*a* and 350*b*.

In various instances, examples can improve infusion coverage estimations by ensuring alignment between inter-operative images prior to image comparison/subtraction. To this end, examples may acquire inter-operative images 310-330 images using the same/similar image sequence parameters and scan/image geometry. Thus, assuming the patient remains stationary during the procedure, inter-operative images 310-330 should be aligned prior to comparison/subtraction. However, to account for any change of position of the patient (and by extension the patient's brain) during the infusion procedure, examples can align one inter-operative image with another prior to image comparison/subtraction (such image alignment is sometimes referred to as "registering" one image to another image). For instance, to account for patient movement between when inter-operative image 310 and inter-operative image 330 were acquired, examples can align inter-operative image 330 with inter-operative image 310. This aligning/registering may comprise estimating a transformation between inter-operative image 330 and inter-operative image 310. By aligning/registering inter-operative image 330 to inter-operative image 310, examples can improve alignment between inter-operative image 330 and inter-operative image 310 prior to image comparison/subtraction, and thus improve infusion coverage estimates based upon such image comparison/subtraction.

FIG. 4 depicts an example flow diagram that may be used to estimate a level of coverage for infusate delivered to a target brain region, in accordance with various examples of the presently disclosed technology.

At operation 402, examples compare a first 3D image of a patient's brain acquired before infusate has been delivered to the patient's brain to a second 3D image of the patient's brain acquired after infusate has been delivered to the patient's brain. In various examples, such a comparison may comprise subtracting the first 3D image of a patient's brain from the second 3D image of the patient's brain (as used herein, image subtraction may refer to a process of subtracting numeric values of voxels of one 3D image from numeric values of voxels of another 3D image—such subtraction can be used to identify differences between the two 3D images). As will be described in conjunction with operation 404, based on this image comparison/subtraction, examples can generate a 3D infusate delivery representation that volumetrically/spatially represents the delivered infusate within the patient's brain.

The first and second 3D images of the patient's brain may be various types of images including MRI images or CT images. In various instances, the first and second 3D images of the patient's brain may be inter-operative images obtained during an infusion procedure. As described above, the first 3D image of the patient's brain may serve as a "baseline/pre-infusate delivery image" for image comparison/subtraction.

As described in conjunction with FIG. 3, in various instances, examples can improve infusion coverage estimations by ensuring alignment between the first and second 3D images of the patient's brain prior to image comparison/subtraction. To this end, examples may acquire the first and second 3D images of the patient's brain using the same/ similar image sequence parameters and scan/image geometry during an infusion procedure. Thus, assuming the patient remains stationary during the infusion procedure, the first and second 3D images of the patient's brain should be aligned prior to image comparison/subtraction. However, to account for any change of position of the patient (and by extension the patient's brain) during the infusion procedure, examples can align the second 3D image of the patient's brain with the first 3D image of the patient's brain prior to image comparison/subtraction (such image alignment is sometimes referred to as "registering" one image to another image). This aligning/registering may comprise estimating a transformation between the second 3D image of the patient's brain and the first 3D image of the patient's brain. By aligning/registering the second 3D image of the patient's brain with the first 3D image of the patient's brain, examples can improve alignment between the second 3D image of the patient's brain and the first 3D image of the patient's brain prior to image comparison/subtraction, and thus improve infusion coverage estimates based upon such image comparison/subtraction.

At operation 404, examples generate a 3D infusate delivery representation based on the image comparison/subtraction of operation 402. The 3D infusate delivery representation may be a computerized 3D representation that volumetrically and spatially represents the delivered infusate within the patient's brain. The delivered infusate within the patient's brain will typically include a volume of delivered infusate located in the target brain region, but in some cases, may also include a volume of delivered infusate located outside the target brain region. Here it should be understood that computerized estimation systems may not be able to determine, from the 3D infusate delivery representation alone, which volumes/portions of the 3D infusate delivery representation correspond to delivered infusate within the target brain region vs. which volumes/portions of the 3D infusate delivery representation correspond to delivered infusate located outside of the target brain region. To help computerized estimation systems with this identification, examples compare the 3D infusate delivery representation to a segmented 3D representation of the patient's brain. As will be described in greater detail in conjunction with operation 406, the segmented 3D representation of the patient's brain may comprise one or more 3D segments/sub-representations that represent various brain structures/regions of the patient, including the target brain region. Here, by "segmenting" a 3D representation of the patient's brain into 3D segments/sub-representations that represent various brain structures/regions, the segmented 3D representation of the patient's brain may effectively identify the various brain structures/regions of the patient, including the target brain region. Thus, by comparing the 3D infusate delivery representation to the segmented 3D representation of the patient's brain, examples can help computerized estimation systems identify/estimate which volumes/portions of the 3D infusate delivery representation correspond to delivered infusate within the target brain region vs. which volumes/portions of the 3D infusate delivery representation correspond to delivered infusate located outside of the target brain region.

As alluded to above at operation 406, examples compare the 3D infusate delivery representation to a segmented 3D representation of the patient's brain. In various examples, comparing the 3D infusate delivery representation to the segmented 3D representation of the patient's brain may comprise combining/overlaying the 3D infusate delivery representation and the segmented 3D representation of the patient's brain. In this way, examples can identify/estimate which volumes/portions of the 3D infusate delivery representation correspond to delivered infusate within the target brain region vs. which volumes/portions of the 3D infusate delivery representation correspond to delivered infusate located outside of the target brain region.

As described above, the segmented 3D representation of the patient's brain may comprise one or more 3D segments/sub-representations that represent various brain structures/regions (e.g., sub-cortical structures such as the putamen, thalamus, etc.), including the target brain region. The 3D segment/sub-representation that represents the target brain region may be referred to as a 3D target brain structure sub-representation. The target brain region may be a region of the patient's brain targeted for drug/infusate delivery. The target brain region may be a specific brain structure (e.g., a sub-cortical structure such as the putamen, thalamus, etc.), a portion/segment of a specific brain structure, or a more general region/volume of the patient's brain.

As described in conjunction with FIGS. 1-2, examples can generate the (patient-specific) segmented 3D brain representation of the patient's brain by adapting a generalized segmented 3D brain representation (i.e., a non-patient-specific segmented 3D representation of the human brain) to patient-specific brain image data commonly acquired in clinical settings (e.g., MRI or CT scans of a patient's brain). In this way, examples of the presently disclosed technology can be easily reproduced across different patients, procedures, sites, etc. Accordingly, examples of the presently disclosed technology may improve upon existing infusion coverage estimation methodologies which are not as easily reproducible.

In some instances, examples may generate the segmented 3D brain representation of the patient's brain by adapting a generalized segmented 3D brain representation directly to the first 3D image of the patient's brain (here the first 3D image of the patient's brain may be an inter-operative image). However, in other instances, examples may generate the segmented 3D brain representation of the patient's brain based on pre-operative imagining data of the patient's brain.

In certain examples, the generalized segmented 3D brain representation described above may comprise a mesh/surface mesh representation. A mesh (or surface mesh) may refer to a representation of a larger domain (e.g., a volume or surface) comprised of smaller discrete cells called mesh elements, and mesh vertices at the junctions of adjacent/adjoining mesh elements. Meshes can be used to compute solutions to equations across individual mesh elements, which then can be used to approximate solutions over the larger domain. For example, meshes can be used to compute volumes contained within 3D closed mesh boundary surfaces. By adapting a generalized segmented 3D (mesh) brain representation to imaging data of a given patient's brain, examples can generate patient-specific segmented 3D (mesh) brain representations.

Accordingly, in certain examples the segmented 3D brain representation of the patient's brain may comprise a 3D mesh representation. In these examples, the various segments/sub-representations of the segmented 3D brain representation of the patient's brain, including the 3D target brain region sub-representation, may be represented as 3D closed mesh boundary surfaces comprised of mesh elements and mesh vertices (the volumes of these 3D closed mesh boundary surfaces may comprise mesh elements and mesh vertices as well). As will be described below, examples can estimate a volume for the target brain region by computing a volume for a 3D closed mesh boundary surface (i.e., the 3D target brain region sub-representation) representing the target brain region. This estimated volume for the target brain region can be compared to an estimated volume for infusate delivered to the target brain region to estimate a level of coverage for delivered infusate within the target brain region.

As described above, comparing the 3D infusate delivery representation to the segmented 3D representation of the patient's brain may comprise combining/overlaying the 3D infusate delivery representation and the segmented 3D representation of the patient's brain (which includes the 3D target brain region sub-representation). In this way, examples can identify/estimate which volumes/portions of the 3D infusate delivery representation correspond to delivered infusate within the target brain region vs. which volumes/portions of the 3D infusate delivery representation correspond to delivered infusate located outside of the target brain region. For instance (and as will be described in greater detail in conjunction with operation 408), examples can estimate a volume for delivered infusate within the target brain region based on an amount of overlap between the 3D infusate delivery representation and the 3D target brain structure sub-representation after they have been combined/overlaid.

Based on the comparison performed at operation 406, at operation 408, examples estimate a level of coverage for delivered infusate within the target brain region. In various instances, this may comprise (1) estimating a volume for delivered infusate within the target brain region based on an amount of overlap between the 3D infusate delivery representation and the 3D target brain region representation after the 3D infusate delivery representation and the segmented 3D representation of the patient's brain have been combined/overlaid; (2) estimating a volume of the target brain region based on the 3D target brain region sub-representation; and (3) estimating the level of coverage for delivered infusate within the target brain region by comparing the estimated volume for delivered infusate within the target brain region to the estimated volume for the target brain region.

As described above, in some cases, all of the delivered infusate may be located within the target brain region. In these cases, the 3D infusate delivery representation may be completely overlapped by the 3D target brain region representation after they have been combined/overlaid. However, in other cases a portion of the delivered infusate may be located outside of the target brain region. In these cases, a portion of the 3D infusate delivery representation will not overlap with the 3D target brain region representation after they have been combined/overlaid.

Examples can use various techniques to estimate the volume for delivered infusate within the target brain region based on the amount of overlap between the 3D infusate delivery representation and the 3D target brain region sub-representation after they have been combined/overlaid. For instance, examples can count the number of voxels shared by the 3D infusate delivery representation and the 3D target brain region sub-representation. The amount overlap between the 3D infusate delivery representation and the 3D target brain region sub-representation may also be estimated using 3D surfaces (e.g., 3D closed mesh boundary surfaces) instead of voxel counting. This could involve estimating a 3D surface for 3D infusate delivery representation (e.g., a 3D closed mesh boundary surface for the 3D infusate delivery representation), and comparing this 3D surface to a 3D surface (e.g., a 3D closed mesh boundary surface) for the 3D target brain region sub-representation.

Examples can also use various techniques to estimate the volume of the target brain region based on the 3D target brain region sub-representation. For instance, where the 3D target brain region sub-representation comprises a 3D closed mesh boundary surface, examples can estimate the volume of the target brain region by computing the volume for the 3D closed mesh boundary surface. For example, a total mesh volume could be computed using signed tetrahedral volumes. One volume may be computed for each mesh triangle, using a common origin to form each tetrahedron.

In other instances (e.g., where the target brain region cannot be represented by a 3D closed boundary surface), examples can estimate the volume of the target brain region by counting the number of voxels comprising the 3D target brain region sub-representation.

Based on comparing the estimated volume for delivered infusate within the target brain region to the estimated volume for the target brain region, examples can use various techniques to estimate the level of coverage for delivered infusate within the target brain region. For instance, examples can divide the estimated volume for delivered infusate within the target brain region by the estimated volume for the target brain region (and multiple by 100%) to obtain a percentage of infusate coverage within the target brain region.

As described above, in some cases a portion of delivered infusate may be located outside of the target brain region. Examples can estimate a volume for delivered infusate located outside of the target brain region by e.g., comparing the 3D infusate delivery representation to the 3D target brain region sub-representation. For instance, where the 3D infusate delivery representation and segmented 3D representation of the patient's brain have been combined/overlaid, examples can count the number of voxels of the 3D infusate delivery representation which are not shared by the 3D target brain region sub-representation. Where the 3D target brain region sub-representation comprises a 3D mesh boundary surface, examples can leverage the surface normals of mesh elements to define the inside of the 3D target brain region sub-representation vs. the outside of the 3D target brain region sub-representation for voxel-counting purposes.

At operation 410, examples provide a notification related to the estimated level of coverage for delivered infusate within the target brain region. In various instances, this operation may further or alternatively comprise providing a notification related to the estimated volume of delivered infusate located outside of the target brain region.

The provided notification may take various forms that visualize estimated infusion coverage for a user/neurosurgeon. In one instance, the notification can visualize estimated infusion coverage using a "traffic light" notion: i.e., red (i.e., complete coverage achieved/stop infusion), yellow (i.e., nearly complete coverage achieved/continue infusion with caution), and green (i.e., incomplete infusion coverage/continue infusion). Here, infusion can be stopped when a certain percentage of coverage for the targeted brain region has been achieved (as indicated by the "red symbol"). As described above, the provided notification may also comprise an notification/alert when delivered infusate is leaking/located outside of the target brain region. Such an alert may comprise, e.g., a recommendation to stop infusion or to adjust the location of the targeting cannula delivering infusate.

Figure 5:
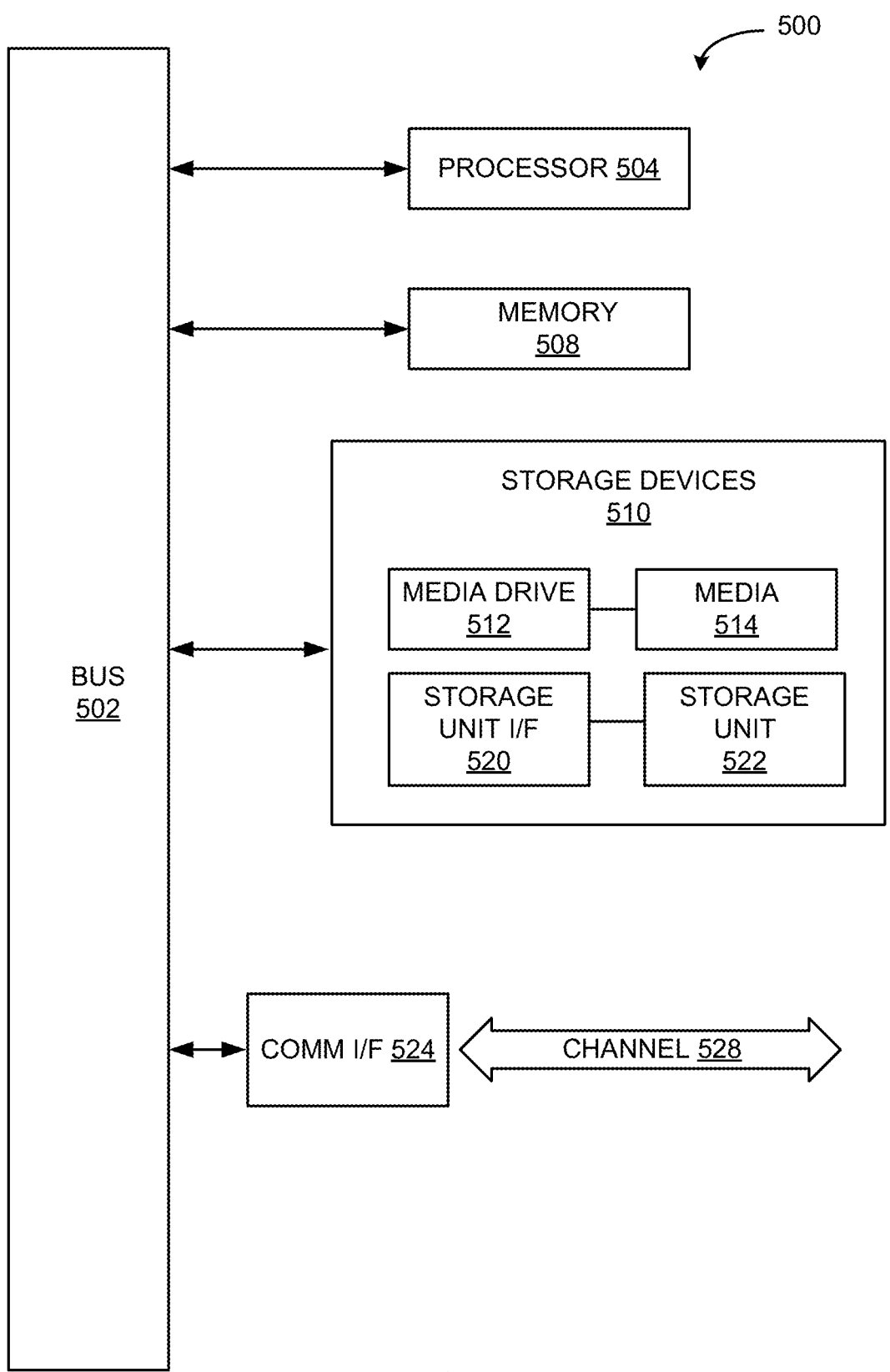
FIG. 5 is an example computing component that may be used to implement various features of examples described in the present disclosure.

As used herein, the terms circuit and component might describe a given unit of functionality that can be performed in accordance with one or more examples of the present application. As used herein, a component might be implemented utilizing any form of hardware, software, or a combination thereof. For example, one or more processors, controllers, ASICs, PLAs, PALs, CPLDs, FPGAs, logical components, software routines or other mechanisms might be implemented to make up a component. Various components described herein may be implemented as discrete components or described functions and features can be shared in part or in total among one or more components. In other words, as would be apparent to one of ordinary skill in the art after reading this description, the various features and functionality described herein may be implemented in any given application. They can be implemented in one or more separate or shared components in various combinations and permutations. Although various features or functional elements may be individually described or claimed as separate components, it should be understood that these features/functionality can be shared among one or more common software and hardware elements. Such a description shall not require or imply that separate hardware or software components are used to implement such features or functionality.

Where components are implemented in whole or in part using software, these software elements can be implemented to operate with a computing or processing component capable of carrying out the functionality described with respect thereto. One such example computing component is shown in FIG. 5. Various examples are described in terms of this example-computing component 500. After reading this description, it will become apparent to a person skilled in the relevant art how to implement the application using other computing components or architectures.

Referring now to FIG. 5, computing component 500 may represent, for example, computing or processing capabilities found within a self-adjusting display, desktop, laptop, notebook, and tablet computers. They may be found in hand-held computing devices (tablets, PDA's, smart phones, cell phones, palmtops, etc.). They may be found in workstations or other devices with displays, servers, or any other type of special-purpose or general-purpose computing devices as may be desirable or appropriate for a given application or environment. Computing component 500 might also represent computing capabilities embedded within or otherwise available to a given device. For example, a computing component might be found in other electronic devices such as, for example, portable computing devices, and other electronic devices that might include some form of processing capability.

Computing component 500 might include, for example, one or more processors, controllers, control components, or other processing devices. Processor 504 might be implemented using a general-purpose or special-purpose processing engine such as, for example, a microprocessor, controller, or other control logic. Processor 504 may be connected to a bus 502. However, any communication medium can be used to facilitate interaction with other components of computing component 500 or to communicate externally.

Computing component 500 might also include one or more memory components, simply referred to herein as main memory 508. For example, random access memory (RAM) or other dynamic memory, might be used for storing information and instructions to be executed by processor 504. Main memory 508 might also be used for storing temporary variables or other intermediate information during execution of instructions to be executed by processor 504. Computing component 500 might likewise include a read only memory ("ROM") or other static storage device coupled to bus 502 for storing static information and instructions for processor 504.

The computing component 500 might also include one or more various forms of information storage mechanism 150, which might include, for example, a media drive 512 and a storage unit interface 520. The media drive 512 might include a drive or other mechanism to support fixed or removable storage media 514. For example, a hard disk drive, a solid-state drive, a magnetic tape drive, an optical drive, a compact disc (CD) or digital video disc (DVD) drive (R or RW), or other removable or fixed media drive might be provided. Storage media 514 might include, for example, a hard disk, an integrated circuit assembly, magnetic tape, cartridge, optical disk, a CD or DVD. Storage media 514 may be any other fixed or removable medium that is read by, written to or accessed by media drive 512. As these examples illustrate, the storage media 514 can include a computer usable storage medium having stored therein computer software or data.

In alternative examples, information storage mechanism 150 might include other similar instrumentalities for allowing computer programs or other instructions or data to be loaded into computing component 500. Such instrumentalities might include, for example, a fixed or removable storage unit 522 and an interface 520. Examples of such storage units 522 and interfaces 520 can include a program cartridge and cartridge interface, a removable memory (for example, a flash memory or other removable memory component) and memory slot. Other examples may include a PCMCIA slot and card, and other fixed or removable storage units 522 and interfaces 520 that allow software and data to be transferred from storage unit 522 to computing component 500.

Computing component 500 might also include a communications interface 524. Communications interface 524 might be used to allow software and data to be transferred between computing component 500 and external devices. Examples of communications interface 524 might include a modem or softmodem, a network interface (such as Ethernet, network interface card, IEEE 802.XX or other interface). Other examples include a communications port (such as for example, a USB port, IR port, RS232 port Bluetooth® interface, or other port), or other communications interface. Software/data transferred via communications interface 524 may be carried on signals, which can be electronic, electromagnetic (which includes optical) or other signals capable of being exchanged by a given communications interface 524. These signals might be provided to communications interface 524 via a channel 528. Channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media. Such media may be, e.g., memory 508, storage unit 520, media 514, and channel 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 500 to perform features or functions of the present application as discussed herein.

It should be understood that the various features, aspects and functionality described in one or more of the individual examples are not limited in their applicability to the particular example with which they are described. Instead, they can be applied, alone or in various combinations, to one or more other examples, whether or not such examples are described and whether or not such features are presented as being a part of a described example. Thus, the breadth and scope of the present application should not be limited by any of the above-described exemplary examples.

Terms and phrases used in this document, and variations thereof, unless otherwise expressly stated, should be construed as open ended as opposed to limiting. As examples of the foregoing, the term "including" should be read as meaning "including, without limitation" or the like. The term "example" is used to provide exemplary instances of the item in discussion, not an exhaustive or limiting list thereof. The terms "a" or "an" should be read as meaning "at least one," "one or more" or the like; and adjectives such as "conventional," "traditional," "normal," "standard," "known." Terms of similar meaning should not be construed as limiting the item described to a given time period or to an item available as of a given time. Instead, they should be read to encompass conventional, traditional, normal, or standard technologies that may be available or known now or at any time in the future. Where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the aspects or functionality described or claimed as part of the component are all configured in a common package. Indeed, any or all of the various aspects of a component, whether control logic or other components, can be combined in a single package or separately maintained and can further be distributed in multiple groupings or packages or across multiple locations.

The terms "optimize," "optimal" and the like as used herein can be used to mean making or achieving performance as effective or perfect as possible. However, as one of ordinary skill in the art reading this document will recognize, perfection cannot always be achieved. Accordingly, these terms can also encompass making or achieving performance as good or effective as possible or practical under the given circumstances, or making or achieving performance better than that which can be achieved with other settings or parameters.

Additionally, the various examples set forth herein are described in terms of exemplary block diagrams, flow charts and other illustrations. As will become apparent to one of ordinary skill in the art after reading this document, the illustrated examples and their various alternatives can be implemented without confinement to the illustrated examples. For example, block diagrams and their accompanying description should not be construed as mandating a particular architecture or configuration.

The invention claimed is:

1. A method, comprising:
subtracting a first 3D image of a patient's brain acquired before infusate has been delivered to the patient's brain from a second 3D image of the patient's brain acquired after infusate has been delivered to the patient's brain;
based on the subtraction, generating a 3D infusate delivery representation, the 3D infusate delivery representation volumetrically representing the delivered infusate within the patient's brain;
comparing the 3D infusate delivery representation to a segmented 3D representation of the patient's brain, wherein the segmented 3D representation of the patient's brain comprises a 3D target brain region sub-representation representing a target brain region of the patient;
based on the comparison, estimating a level of coverage for delivered infusate within the target brain region; and
providing a notification related to the estimated level of coverage for delivered infusate within the target brain region.

2. The method of claim 1, wherein comparing the 3D infusate delivery representation to the segmented 3D representation of the patient's brain comprises overlaying the 3D infusate delivery representation and the segmented 3D representation of the patient's brain.

3. The method of claim 2, wherein estimating the level of coverage for delivered infusate within the target brain region comprises:
estimating a volume for delivered infusate within the target brain region based on an amount of overlap between the 3D infusate delivery representation and the 3D target brain region sub-representation after the 3D infusate delivery representation and the segmented 3D representation of the patient's brain have been overlaid;
estimating a volume of the target brain region based on the 3D target brain region sub-representation; and
estimating the level of coverage for delivered infusate within the target brain region by comparing the estimated volume for delivered infusate within the target brain region to the estimated volume for the target brain region.

4. The method of claim 3, wherein estimating the volume for delivered infusate within the target brain region based on the amount of overlap between the 3D infusate delivery representation and the 3D target brain region sub-representation comprises counting a number of voxels shared by the 3D infusate delivery representation and the 3D target brain region sub-representation after the 3D infusate delivery representation and the segmented 3D representation of the patient's brain have been overlaid.

5. The method of claim 3, wherein estimating the volume of the target brain region comprises counting a number of voxels that comprise the 3D target brain region sub-representation.

6. The method of claim 1, wherein the first 3D image of the patient's brain and second image 3D of the patient's brain are acquired using the same image sequence parameters and image geometry.

7. The method of claim 1, further comprising, prior to subtracting the first 3D image of the patient's brain from the second 3D image of the patient's brain, aligning the second 3D image of the patient's brain with the first 3D image of the patient's brain to account for a change in position of the patient between acquisition of the first 3D image of the patient's brain and acquisition of the second 3D image of the patient's brain.

8. A non-transitory computer-readable storage medium including instructions that, when executed by at least one processor of a computing system, cause the computing system to perform a method comprising:
 subtracting a first 3D image of a patient's brain acquired before infusate has been delivered to the patient's brain from a second 3D image of the patient's brain acquired after infusate has been delivered to the patient's brain;
 based on the subtraction, generating a 3D infusate delivery representation, the 3D infusate delivery representation volumetrically representing the delivered infusate within the patient's brain;
 comparing the 3D infusate delivery representation to a segmented 3D representation of the patient's brain, wherein the segmented 3D representation of the patient's brain comprises a 3D target brain region sub-representation representing a target brain region of the patient;
 based on the comparison, estimating a volume of delivered infusate located outside of the target brain region; and
 providing a notification related to the estimated volume of delivered infusate located outside of the target brain region.

9. The non-transitory computer-readable medium of claim 8, wherein the method further comprises:
 based on the comparison, estimating a level of coverage for delivered infusate within the target brain region; and
 providing a notification related to the estimated level of coverage for delivered infusate within the target brain region.

10. The non-transitory computer-readable medium of claim 8, wherein comparing the 3D infusate delivery representation to the segmented 3D representation of the patient's brain comprises overlaying the 3D infusate delivery representation and the segmented 3D representation of the patient's brain.

11. The non-transitory computer-readable medium of claim 10, wherein estimating the level of coverage for delivered infusate within the target brain region comprises:
 estimating a volume for delivered infusate within the target brain region based on an amount of overlap between the 3D infusate delivery representation and the 3D target brain region sub-representation after the 3D infusate delivery representation and the segmented 3D representation of the patient's brain have been overlaid;
 estimating a volume of the target brain region based on the 3D target brain region sub-representation; and
 estimating the level of coverage for delivered infusate within the target brain region by comparing the estimated volume for delivered infusate within the target brain region to the estimated volume for the target brain region.

12. The non-transitory computer-readable medium of claim 11, wherein estimating the volume for delivered infusate within the target brain region based on the amount of overlap between the 3D infusate delivery representation and the 3D target brain region sub-representation comprises counting a number of voxels shared by the 3D infusate delivery representation and the 3D target brain region sub-representation after the 3D infusate delivery representation and the segmented 3D representation of the patient's brain have been overlaid.

13. The non-transitory computer-readable medium of claim 10, wherein estimating the volume of delivered infusate located outside of the target brain region comprises estimating the volume of delivered infusate located outside of the target brain region based on an amount of overlap between the 3D infusate delivery representation and the 3D target brain region sub-representation after the 3D infusate delivery representation and the segmented 3D representation of the patient's brain have been overlaid.

14. The non-transitory computer-readable medium of claim 13, wherein estimating the volume for delivered infusate located outside of the target brain region based on the amount of overlap between the 3D infusate delivery representation and the 3D target brain region sub-representation comprises counting a number of voxels of the 3D infusate delivery representation that are not shared with the 3D target brain region sub-representation after the 3D infusate delivery representation and the segmented 3D representation of the patient's brain have been overlaid.

15. The non-transitory computer-readable medium of claim 8, wherein the 3D target brain region sub-representation comprises a 3D closed mesh boundary surface.

16. A system comprising:
 one or more processing resources; and
 a non-transitory computer-readable medium, coupled to the one or more processing resources, having stored therein instructions that when executed by the one or more processing resources cause the system to:
  compare a first 3D image of a patient's brain acquired before infusate has been delivered to the patient's brain to a second 3D image of the patient's brain acquired after infusate has been delivered to the patient's brain;
  based on the image comparison, generate a 3D infusate delivery representation, the 3D infusate delivery representation volumetrically representing the delivered infusate within the patient's brain;
  overlay the 3D infusate delivery representation and the segmented 3D representation of the patient's brain, wherein:
   the segmented 3D representation of the patient's brain comprises one or more 3D sub-representations, a given 3D sub-representation representing a given brain region of the patient, and
   one of the one or more 3D sub-representations comprises a 3D target brain region sub-representation representing a target brain region of the patient;
  based on the overlaid 3D infusate delivery representation and segmented 3D representation of the patient's brain, estimate a level of coverage for delivered infusate within the target brain region; and
  provide a notification related to the estimated level of coverage for delivered infusate within the target brain region.

17. The system of claim 16, wherein the image comparison comprises subtracting the first 3D image of the patient's brain from the second 3D image of the patient's brain.

18. The system of claim 16, wherein the first 3D image of the patient's brain and the second 3D image of the patient's brain are acquired using the same image sequence parameters and image geometry.

19. The system of claim 16, wherein estimating the level of coverage for delivered infusate within the target brain region comprises:
 estimating a volume for delivered infusate within the target brain region based on an amount of overlap between the 3D infusate delivery representation and the 3D target brain region sub-representation after the 3D infusate delivery representation and the segmented 3D representation of the patient's brain have been overlaid;
 estimating a volume of the target brain region based on the 3D target brain region sub-representation; and estimating the level of coverage for delivered infusate within the target brain region by comparing the estimated volume for delivered infusate within the target brain region to the estimated volume for the target brain region.

20. The system of claim 16, wherein the segmented 3D representation of the patient's brain comprises a 3D mesh representation and the 3D target brain region sub-representation comprises a 3D closed mesh boundary surface.

* * * * *